(12) United States Patent
Pérez et al.

(10) Patent No.: US 7,784,947 B2
(45) Date of Patent: Aug. 31, 2010

(54) CATARACT SURGERY MICROSCOPY SYSTEM AND METHOD THEREFOR

(75) Inventors: Michel Pérez, Dijon (FR); Daniel Kolster, Oberkochen (DE); Gerhard Gaida, Aalen (DE); Peter Reimer, Ellwangen (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 1914 days.

(21) Appl. No.: 10/459,858

(22) Filed: Jun. 12, 2003

(65) Prior Publication Data

US 2004/0102799 A1 May 27, 2004

(30) Foreign Application Priority Data

Jun. 13, 2002 (DE) ................ 102 26 382

(51) Int. Cl.
*A61B 3/10* (2006.01)
(52) U.S. Cl. .................. 351/211; 351/204; 351/216
(58) Field of Classification Search ........... 351/211, 351/200, 212, 240, 204–207, 209, 210, 215, 351/216; 623/6.32–6.36, 6.12; 606/4–6
See application file for complete search history.

(56) References Cited

U.S. PATENT DOCUMENTS

| 4,490,022 | A |   | 12/1984 | Reynolds |   |
|---|---|---|---|---|---|
| 4,964,715 | A |   | 10/1990 | Richards |   |
| 5,054,907 | A |   | 10/1991 | Sklar et al. |   |
| 5,116,782 | A | * | 5/1992 | Yamaguchi et al. | 250/492.3 |
| 5,801,807 | A |   | 9/1998 | Satake et al. |   |
| 6,190,012 | B1 | * | 2/2001 | Ishikura | 351/212 |
| 6,224,213 | B1 |   | 5/2001 | Kobayashi |   |
| 6,257,723 | B1 |   | 7/2001 | Sarver et al. |   |
| 6,382,796 | B1 |   | 5/2002 | Ban |   |
| 2003/0142271 | A1 | * | 7/2003 | Ross et al. | 351/212 |

FOREIGN PATENT DOCUMENTS

| DE | 9301448 | U1 |   | 3/1993 |
|---|---|---|---|---|
| DE | 44 17 273 | C2 |   | 12/1997 |
| DE | 197 10 906 | A1 |   | 9/1998 |
| DE | 298 09 759 | U1 |   | 9/1998 |
| DE | 198 56 847 | A1 |   | 6/1999 |
| EP | 0882438 | A |   | 12/1998 |
| JP | 08-066369 |   | * | 8/1994 |
| JP | 11169283 | A |   | 6/1999 |

OTHER PUBLICATIONS

Ravalico, Giuseppe, "Capsulorhexis Size and Posterior Capsule Opacification", J. Cataract Refract Surg., vol. 22, pp. 98-103, Jan./Feb. 1996.

(Continued)

*Primary Examiner*—Ricky L Mack
*Assistant Examiner*—Brandi N Thomas
(74) *Attorney, Agent, or Firm*—Potomac Patent Group PLLC (57) ABSTRACT

A cataract surgery microscopy system is provided which comprises a microscopy optics for producing an image of an object plane of the microscopy optics and a pattern generator for generating a pattern superimposed on the image, said pattern generator being provided to generate a circular pattern having an adjustable diameter.

20 Claims, 4 Drawing Sheets

OTHER PUBLICATIONS

Spalton, David J., "Posterior Capsular Opacification After Cataract Surgery", Eye 13, pp. 489-492 (1999).

Kreiner, Christine, "Intraokularlinsen—Aktueller Stand", der Augenspieger 7-8/01, pp. 20-29.

Lane. S, et al., "Material and Design: Setting New Standards in Clinical Performance—A Roundtable Discussion", Supplement to Opthalmology Times, vol. 26, Jul. 1, 2002.

3D Vision Systems, "Innovative Digital Microsurgical Workstation Previewed at ASCRS," Press Releases, Irvine, CA, Apr. 26, 2004.

European Patent Office Search Report for EP 03 01 3248 mailed Oct. 30, 2007.

European Patent Office Search Report for EP 03 01 3248 mailed Oct. 30, 2007.

* cited by examiner

CATARACT SURGERY MICROSCOPY SYSTEM AND METHOD THEREFOR

FIELD OF THE INVENTION

The invention relates to a cataract surgery microscopy system, a method for preparing an operation in a cataract surgery and a method for performing a cataract surgery.

BACKGROUND OF THE INVENTION

In a cataract surgery a natural lens of the human eye in which a cataract has developed is replaced by an artificial lens. This is a microsurgical operation performed by a surgeon using a surgical microscope for observation. Entering through the sclera or cornea, an incision is made in the capsule sac within the inner margin of the iris and without the latter being injured. By this incision, on the one hand, the endogenous natural lens is removed by suction, for example, after ultrasonic shattering and, on the other hand, the artificial lens is inserted.

Conventionally, the incision in the capsule sac is made by the surgeon by his naked eye, namely such that the incision takes a zigzag or approximately circular course around a center of the inner margin of the iris.

There are grounds for supposing that certain complications are less likely to occur as long-term consequences of the cataract surgery if the incision in the capsule sac has a substantially circular configuration, the diameter of which is adapted to the diameter of the artificial lens to be inserted.

SUMMARY OF THE INVENTION

The present invention has been accomplished taking the above problems into consideration.

It is an object of the present invention to provide a cataract surgery microscopy system, a method for preparing an operation in a cataract surgery and a method for performing a cataract surgery which make it easier for the surgeon to perform this task.

According to a first aspect of the invention a cataract surgery microscopy system is provided which comprises a microscopy optics for producing an image of an object plane of the microscopy optics and a pattern generator for generating a pattern superimposed on the image. The pattern generator is provided to generate a ring pattern with at least one adjustable diameter.

In introducing the incision into the capsule sac, a surgeon can employ the microscopy system and in doing so, align the microscopy system relative to the operated eye such that the capsule sac and iris are disposed approximately in the object plane of the microscopy optics so that he can observe the image thereof through the microscopy optics. He can adjust the microscopy system in such a manner that the generated ring pattern becomes visible within the inner margin of the iris, and he introduces the incision into the capsule sac along the ring pattern. Hence, the ring pattern helps to form an incision having a desired configuration.

According to an embodiment of the invention the ring pattern may be a circular pattern having one single diameter independent of the orientation. However, the pattern may be also oval and have a maximum and a minimum diameter of the kind of an ellipse. However, the ring pattern may be also a pattern, which is composed of polygon pieces. It is important in this respect that the visible impression the surgeon receives from the ring pattern is suitable for helping him to guide the cutting tool in performing the incision.

The ring pattern diameters are set such that the shape of the correspondingly performed incision is adapted to a shape of a lens to be inserted into the capsule sac.

Preferably one of the diameters of the incision, preferably the maximum diameter, corresponds to about 0.5 to 0.6 times, 0.6 to 0.7 times, 0.7 to 0.8 times, 0.8 to 0.9 times or 0.9 to 1.0 times the diameter of the lens to be inserted.

The microscopy optics, for example, may be a conventional surgical stereomicroscope. The pattern generator preferably comprises a projector to feed the pattern into a beam path of the microscopy optics, so that a superposition of the image of the object plane and the pattern can be produced in a simple manner for the surgeon.

To facilitate an alignment of the ring pattern in the image relative to the capsule sac, the pattern generator is preferably provided to further generate a reference pattern comprising a plurality of subpatterns which are spaced from a center of the reference pattern each at an equal adjustable distance. The surgeon can set the distance approximately such that it corresponds in the image to the radius of the inner margin of the iris, and he can further align the microscopy optics relative to the eye such that the subpatterns are each disposed near the inner margin of the iris or substantially superimposed thereon.

According to an embodiment of the invention it is further provided for that the center of the reference pattern coincides with a central point of the ring pattern, so that the incision made along the circular pattern is also formed centrically with respect to the iris.

According to an embodiment of the invention the pattern generator includes interfaces to input the diameters of the ring pattern and to input the distance of the subpatterns of the reference pattern from the center thereof. As the diameter of the incision is adapted to the diameter of the lens to be inserted, in most cases the at least one diameter of the ring pattern is set already before the operation starts and can be inputted in the system, for example, via a keyboard.

The inner diameter of the iris of the eye is in most cases not pre-determined and depends on various parameters such as a medication of the patient. Accordingly, for adjusting the distance of the subpatterns of the reference pattern from the center thereof, it is advantageous to provide an interface, the operation of which is easy for the surgeon or a person preparing the operation. To adjust the distance, the interface preferably comprises an actuator mounted on a housing body of the microscopy optics.

According to a further aspect the invention provides a method for preparing an operation in a cataract surgery comprising generating a microscopic image in a manner that at least an inner margin of an iris of an eye to be operated is visible in the image, and furthermore providing a ring pattern in the image such that the ring pattern represents an extension of an incision to be introduced into a skin of a capsule sac of the eye.

According to a still further aspect, the invention provides a method for performing a cataract surgery, said method comprising generating a microscopic image of a capsule sac of an eye to be operated, providing a ring pattern in the image and introducing an incision into the skin of the capsule sac along the circular pattern.

The forgoing, and other features, and advantages of the invention will be more apparent from the following detailed description of preferred embodiments of the invention with reference to the accompanying drawings.

DETAILED DESCRIPTION

Figure 1:
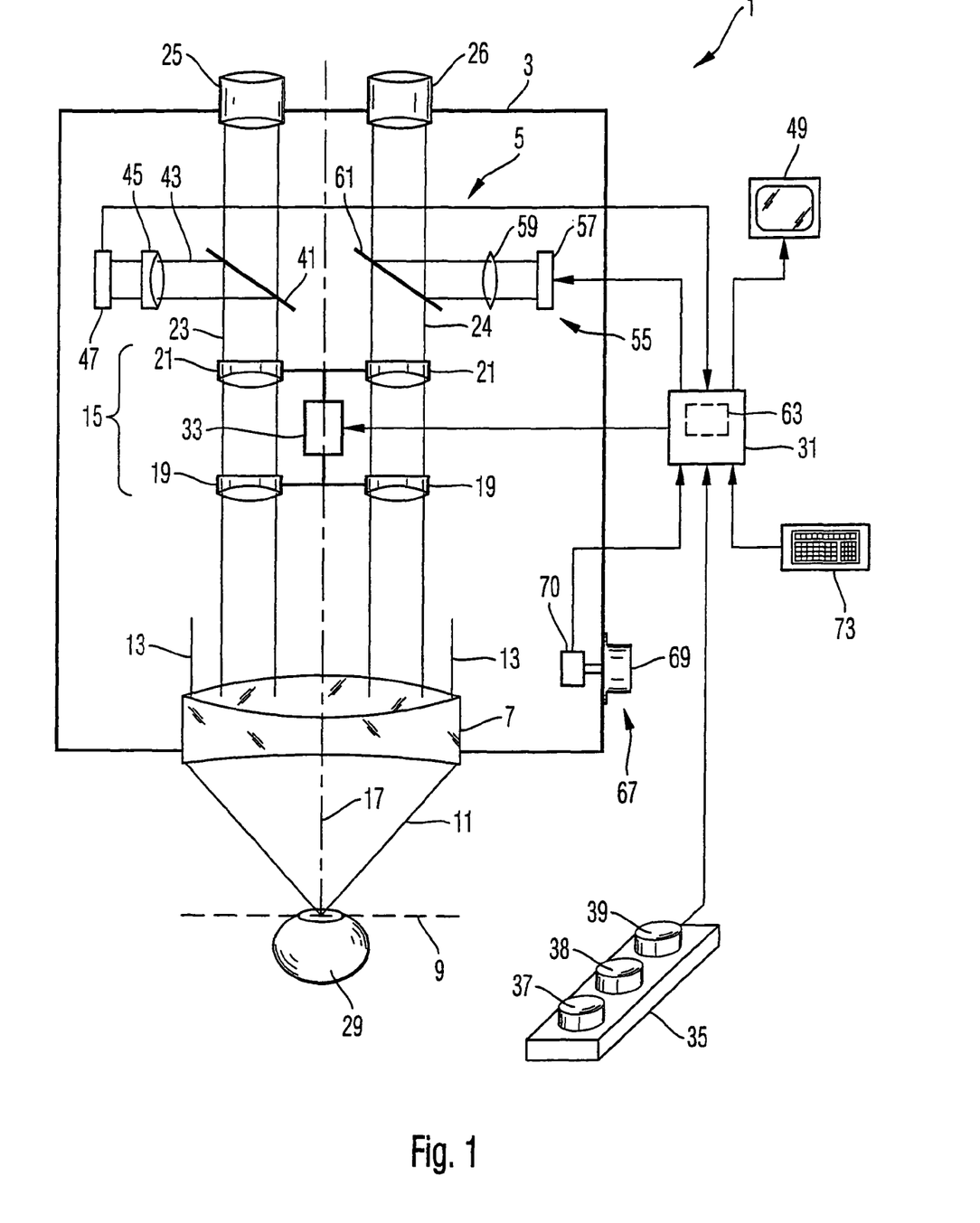
FIG. 1 is a schematic representation of an embodiment of a cataract surgery microscopy system according to the invention.

A cataract surgery microscopy system 1 is schematically shown in FIG. 1. Said system comprises a housing body 3 to accommodate a microscopy optics 5. The microscopy optics 5 comprises a microscopy objective 7 transforming an object-side divergent beam bundle 11 issuing from an object plane 9 of the objective 7 to an image-side parallel beam bundle 13. A double zoom system 15 comprising a lens group 19 and 21 adapted to be displaced along an optical axis 17 of the objective 7 feeds two partial beam bundles 23 and 24 out therefrom, which are supplied to oculars 25 and 26, respectively, through which the surgeon can look with his left and right eyes to observe an image of the object plane 9.

To perform a cataract operation, the surgeon places the microscopy system 1 in front of an eye 29 of a patient on which the operation is to be performed. The surgeon first provides an access to a capsule sac of the eye, for example, by introducing corresponding incisions into a sclera or cornea of the eye 29. Then, the incision is prepared at the capsule sac. For this purpose, the microscopy system 1 comprises a controller 31, for example, a personal computer for controlling a motor 33 for displacing the lens groups 19 and 21 of the zoom system 15, and thus, for changing a magnification of the microscopy optics 5. For control of the motor 33, the controller 31 receives commands from a control panel 35 having press buttons 37, 38 and 39 adapted to be actuated by the surgeons foot or the foot of the person who prepares the incision at the capsule sac. Upon pressing button 37, the controller 31 controls motor 33 so as to increase the magnification of the microscopy optics 35. Upon pressing button 38, the magnification of the microscopy optics is decreased accordingly.

The microscopy optics 1 further comprises a semitransparent mirror 41 which is arranged in the partial beam bundle 23 to feed out therefrom a beam bundle 43 which is directed via an adapter optics 45 to a camera chip 47 so as to produce an image of object plane 9 thereon. Images taken by the camera chip 47 are read out by the controller 31 and displayed on a screen 49. Consequently, the image of the object plane 9 visible on the screen 49 is identical with the image perceived by an observer, when he looks through the ocular 25.

By actuating buttons 37 and 38, the person preparing the incision can then change the magnification and align the optical microscopy system 1 relative to the eye 29 such that the operation field is imaged by the microscopy system 5 at an appropriate size and displayed on the screen 49, respectively.

Figure 2:
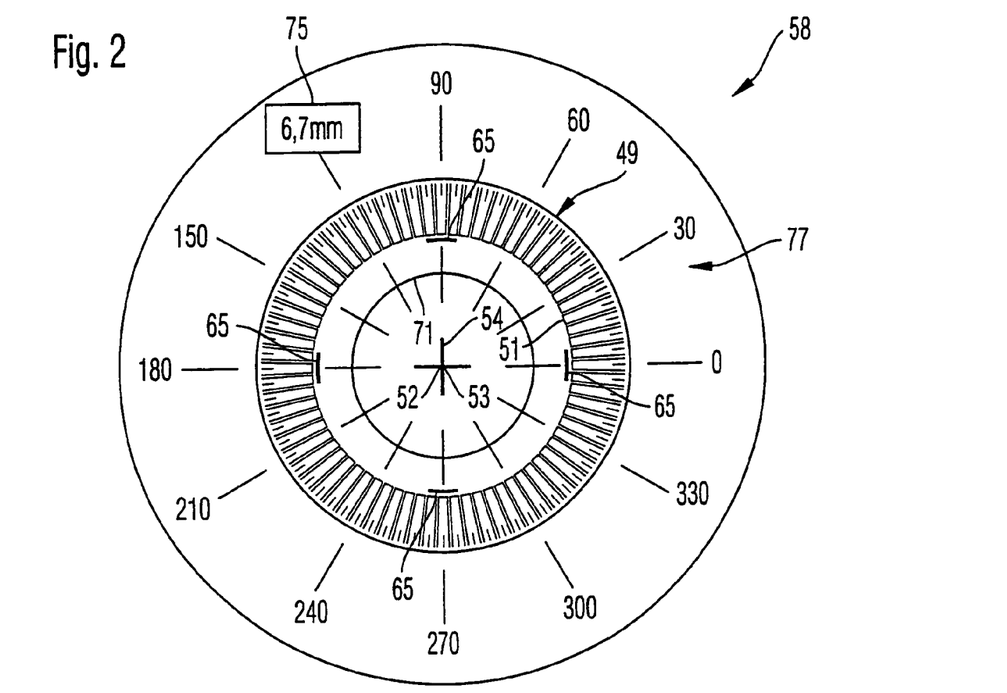
FIG. 2 is a representation of an image produced by the microscopy system of FIG. 1.

FIG. 2 schematically shows an example of a thus produced image 58. In the figure, reference numeral 49 designates an iris of the eye 29 having an inner margin 51 and a center 53.

The microscopy optics 1 further comprises a projector 55 having a display means 57, for example a LCD-display, a projection optics 59 and a semitransparent mirror 61. The semitransparent mirror 61 is disposed in the partial beam bundle 24 and feeds into the partial beam bundle 24 a pattern which is displayed by display means 57 and projected by the optics 59 such that it is perceived as being superimposed on the image of the object plane 9, when looking through the ocular 26. The pattern displayed by display means 57 is generated by a pattern generator 63 in the controller, the controller 31 also superimposing said pattern on the image which is displayed on the screen 49.

The pattern generated by the pattern generator 63 comprises a reference pattern which is composed of four subpatterns 65. In FIG. 2, the subpatterns 65 are spaced at equal distances from a center 52 and form parts of a circle around said center 52 which are spaced at equal distances in circumferential direction. The distance between the subpatterns 65 and the center 53 is adjustable and is read in by the controller 31 via an interface 67, which comprises a rotary knob 69 mounted on the housing body 3 and a rotary position indicator 70 whose position signal is read out by the controller 31. By actuating the rotary knob 69, the person preparing the operation adjusts the distance of the subpatterns 65 from the center 52 so that the subpatterns 65 are disposed close to and symmetrically to the inner margin 51 of the iris 49 of the eye 29. In this adjustment, the microscopy optics 5 is then also disposed relative to the eye 29 such that the center 52 of the reference pattern coincides with its subpatterns with the center 53 of the iris 49, i.e. the microscopy optics 5 is centered with respect to the iris 49.

The pattern generator 63 further generates a ring pattern which in the embodiment described hereinbefore has the shape of a circular pattern 69, the central point of which also coincides with the center 53. A radius of the circular pattern 69 is 6.7 mm, and was read in the controller 31 by the person preparing the operation via a keyboard 73. The value of 6.7 mm corresponds to 0.8 times a diameter of the artificial lens to be inserted into the capsule sac, and is also indicated numerically in the image in a field 75 of the pattern generator 63.

Furthermore, the pattern generator 63 also generates an angular arc pattern 77 from which angular positions around the center 53 in the circumferential direction can be recognised.

An operating mode of the pattern generator 63 is adjustable by actuating the press button 39. In a first operating mode, the pattern generator 63 only generates the circular pattern 71 and no further patterns, this means it does not generate the reference pattern 65 and the angular arc pattern 77. In a second operating mode, the pattern generator 63 only generates the circular pattern 71 and a cross 54 in the center 53. In a third operating mode, the pattern generator 63 only generates the circular pattern 71 and the reference pattern comprising the subpatterns 65. In a fourth operating mode, the pattern generator 63 only generates the circular pattern 71, the reference pattern comprising the subpatterns 65, and the cross pattern 54. In a fifth operating mode, the pattern generator generates all of the previously described patterns i.e. circular pattern 71, reference pattern comprising the subpatterns 65, cross pattern 54 and angular arc pattern 77. In a sixth operating mode, the pattern generator 63 generates none of the patterns indicated in the fifth operating mode, and consequently, the surgeon receives an image of the operation field free of any patterns fed into the beam path. Whenever the press button 39 is actuated, the pattern generator 63 is switched sequentially from one operating mode to the next.

In doing so, the patterns 65 and 71 are generated by the pattern generator 63 such that their sizes scale with the magnification of the microscopy optics adjusted by the motor 33. Hence, even if the magnification of the microscopy optics 5 changes, a relative size of the iris 49 and patterns 65 and 71, respectively, is maintained. In this connection it is possible to also scale the angular arc pattern 77 with the magnification, or not to scale the angular arc pattern 77 and display the latter at a constant size independent of the adjusted magnification.

After the preparation of the operation as described hereinbefore, an image is visible in the ocular 26 and on the screen 49, respectively, as is schematically shown in FIG. 2.

Then the surgeon can introduce the incision into the capsule sac by looking through the oculars 25 and 26 and perform the incision along the circular pattern 71 shown to him in the ocular 26. Subsequently, through the opening formed in the capsule sac, he will, for example by ultrasonics, shatter the existing natural lens and remove it by suction, and insert the artificial intraocular lens into the capsule sac through the formed opening. With the help of the circular pattern 71 indicated in the image, the surgeon succeeded in performing an incision adapted to the diameter of the artificial lens, so that the probability of later complications is reduced.

Figures 3, 4:
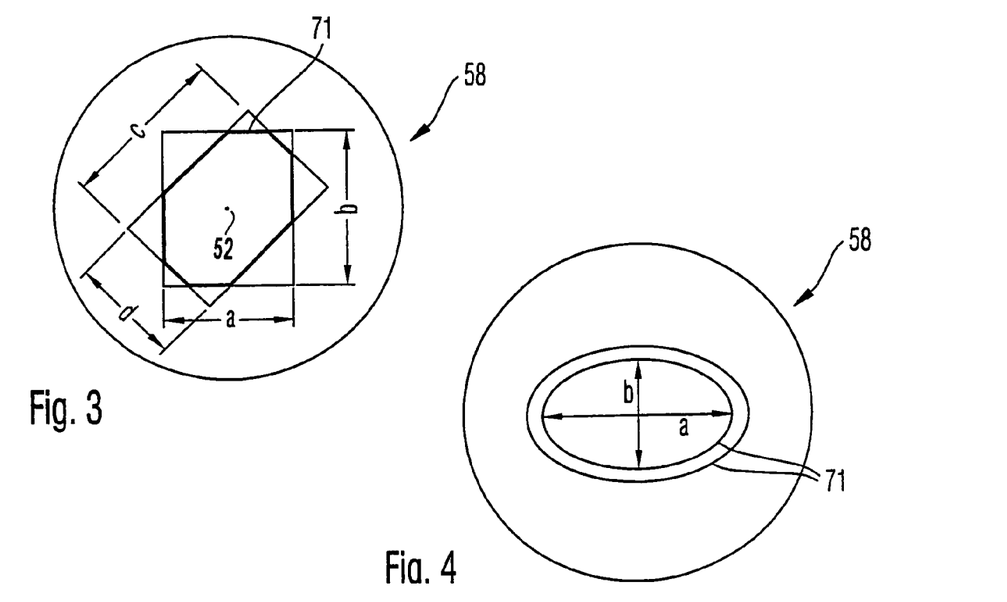
FIG. 3 is a variant of a ring pattern shown in FIG. 2.
FIG. 4 is a further variant of the ring pattern shown in FIG. 2.

In the embodiment described hereinbefore, the ring pattern superimposed on the image is a circular pattern. However, it is also possible, to present the surgeon, for example, a polygon pattern as a help for guiding the incision. An example for this is schematically shown in FIG. 3. Here the polygon results as an octagon from the superimposition of two rectangles. The rectangles have different edge lengths and diameters, respectively, a, b and c, d.

A further variant of a ring pattern is schematically shown in FIG. 4, where the ring pattern is composed of two ellipses, which are spaced from each other at a small radial distance. In this case, the surgeon can introduce the incision, for example, into the space between the two ellipses.

It is also possible that the pattern generator does not permanently indicate the ring pattern as a whole, but indicates individual patterns one after the other. Particularly, it is possible that the pattern generator generates a "light spot" which moves along the contour of the ring pattern to scan the latter within a period of, for example 5 seconds.

Figure 5:
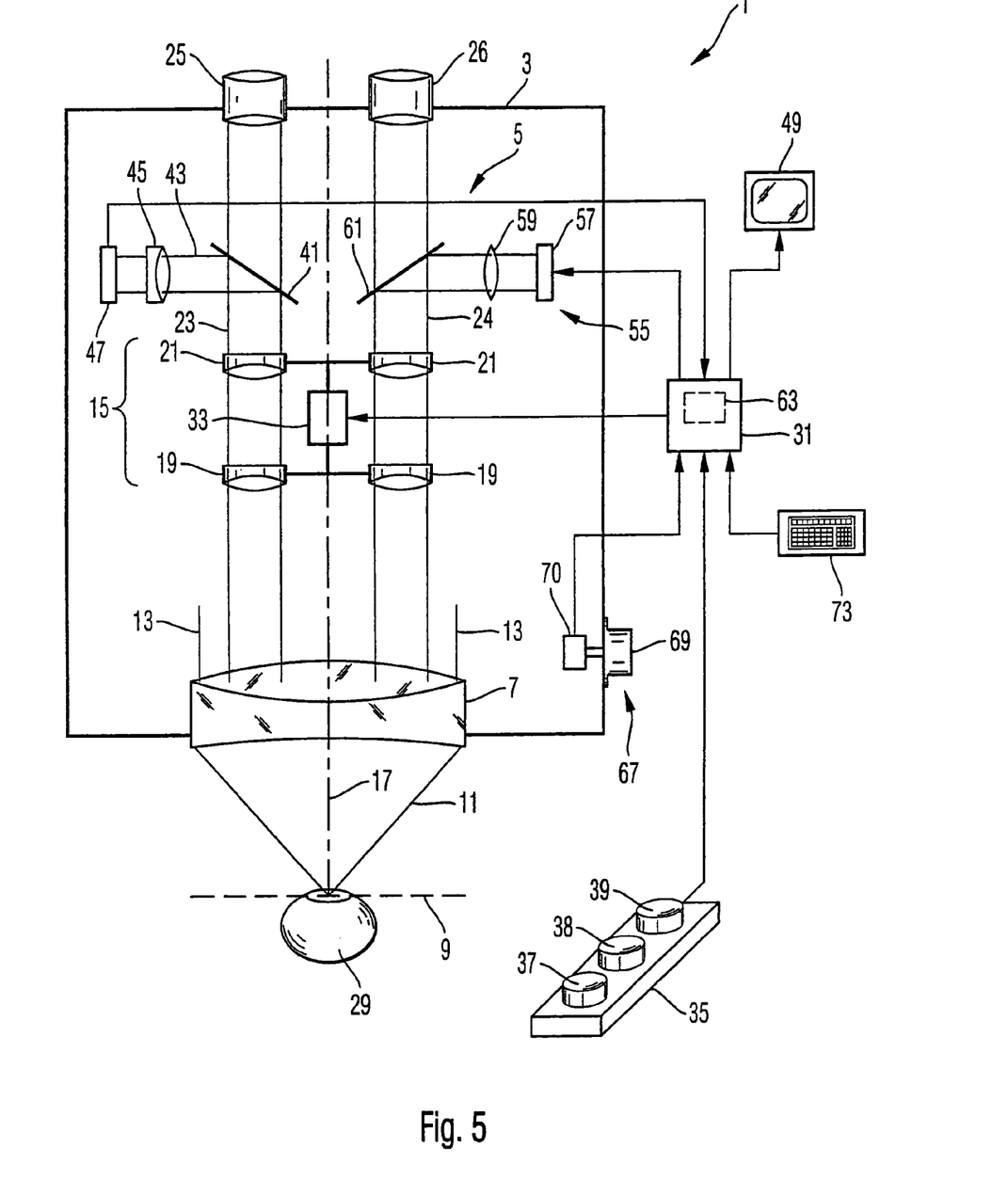
FIG. 5 is a variant of the embodiment shown in FIG. 1.

FIG. 5 shows a further variant of the embodiment explained with reference to FIG. 1. The cataract surgery microscopy system 1 as schematically shown in FIG. 5 resembles to a large extent the system shown in FIG. 1. However, it differs therefrom, in that the pattern generator does not project the pattern 71 towards the ocular 26, but oppositely feeds the pattern into the partial beam bundle 24 such that an image of the pattern is generated in the object plane 9. Consequently, the pattern 71 is projected onto an area surrounding the capsule sac to be operated and as a result of a backscatter of this area, the surgeon perceives a brightly shining area there, when he observes the capsule sac through the microscopy optics, which represents the pattern 71. In this case, he can also use the pattern 71 for orientation to introduce the incision into the capsule sac.

Figure 6:
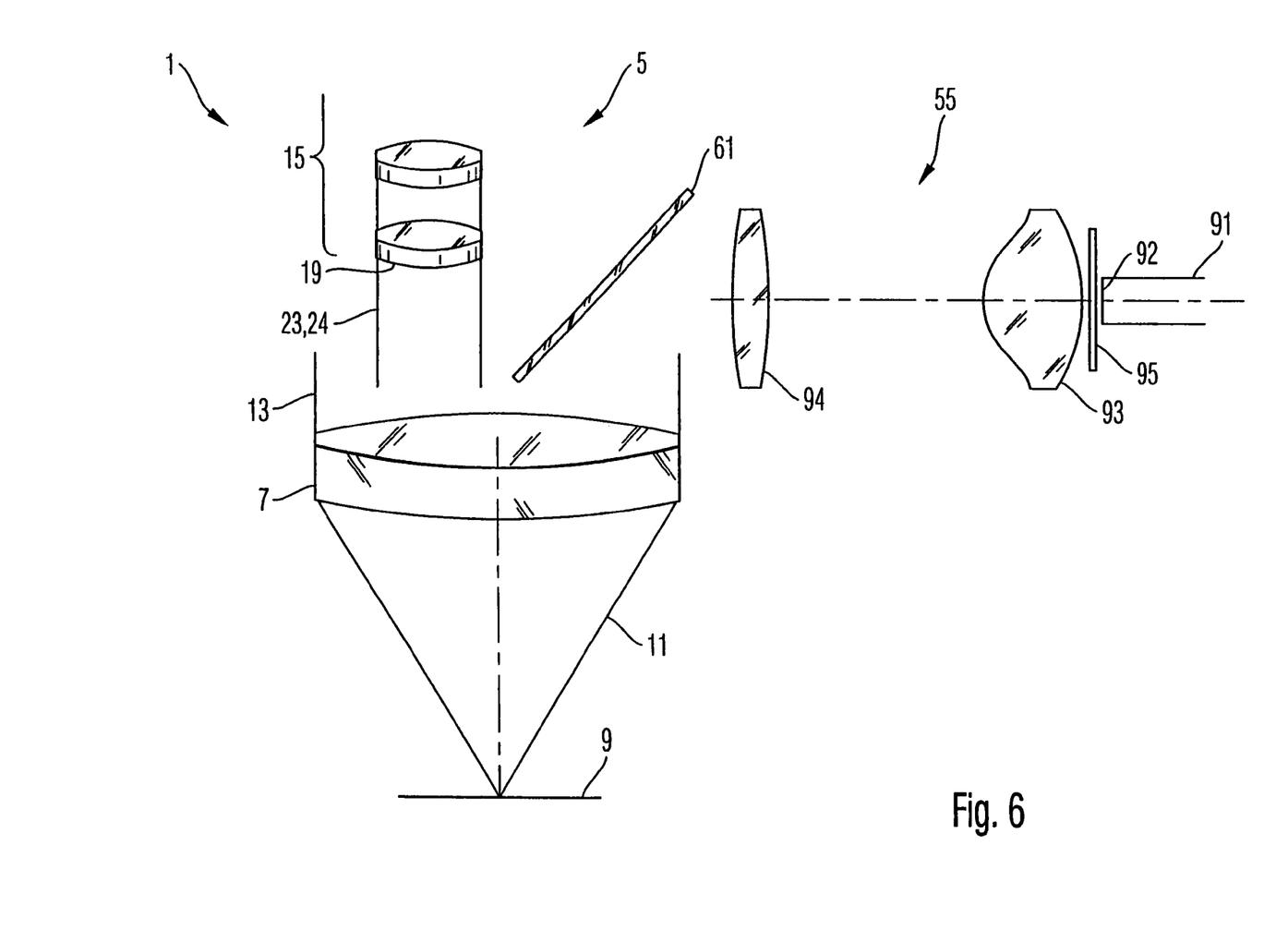
FIG. 6 is a variant of a detail of the embodiment shown in FIG. 5.

In FIG. 6a detail of a variant of the embodiment described with reference to FIG. 5 is schematically shown. In this case, the ring pattern is not fed into a microscopy optics 5 of a cataract surgery microscopy system 1 through one of the partial beam bundles 23, 24 directed to oculars of the microscopy system 1 not shown in FIG. 6. Independently of said partial beam bundles 23, 24 the patterns are fed directly into a beam path of an image-side beam bundle 13. A projection system 55 of the microscopy system 1 as shown in FIG. 6, for example comprises a light guide fibre bundle 91 with the aid of which light is usually supplied for illumination to an object plane 9 of the microscopy optics 5. Light emerges from one end 92 of the light guide fibre bundle 91 and is collimated by aspherical lens 93 as well as a further lens 94 and directed to a path-folding mirror 61, which feeds the collimated light into the beam bundle 13, though in a direction towards the objective 7. The light passes through the objective 7 and is directed towards the object plane 9.

Between the end 92 of the light guide fibre bundle 91 and the aspherical lens 93, there is disposed a LCD-display 95 which is controlled by a computer not shown in FIG. 6. The optics comprising aspherical lens 93, lens 94 and objective 7 is designed such that a pattern displayed on the LCD-display 95 is imaged onto the object plane 9 by the light emerging from the light guide fibre bundle 91. Hence, there is produced in the object plane 9 an image of the pattern displayed on LCD-display 95. When the computer generates with the aid of a pattern generator contained therein the ring pattern explained in connection with the embodiments described hereinbefore, such pattern is projected onto the object plane 9. If the eye to be operated and its capsule sac are placed there, since the capsule sac has scattering structures, back reflections will be generated which can be perceived by the surgeon when he looks through the microscopy system 1, and which help the surgeon to perform the incision to be introduced.

It is also possible to dispose LCD-display 95 at a place different from that shown in FIG. 6 in the beam path of the illuminating beam, for example between the lenses 93 and 94 or between the lens 94 and the mirror 61.

In the method described hereinbefore and the microscopy optics, the center 53 of the inner margin 51 of the iris 49 and the center 52 of the reference pattern with its subpatterns 65, respectively, is centered with respect to the central point of the circular pattern 71 to perform the incision so as to be centered with respect to the iris. However, it is also possible to dispose the central point of the circular pattern 71 somewhat outside of the center 52 of the subpatterns 65 and the inner margin 51 of the iris 49, respectively.

Hereinbefore, the ring pattern 71 was represented by a continuous line. However, for the representation of the ring pattern 71, it is also possible to use a discontinuous line such as a broken line or dash-dot line.

Furthermore, hereinbefore the reference pattern was indicated by only four subpatterns 65. However, it is also possible to employ a larger number of subpatterns, each of which is spaced from the center point of the reference pattern at an equal distance. In particular, it is possible to represent the reference pattern by a continuous circular line.

In the embodiment described hereinbefore, the diameter of the reference pattern comprising the subpatterns 65 is adjusted through keyboard 73. However, it is also possible for the adjustment of this diameter, to provide an actuator on the main body 3 of the microscopy optics similar to what was described for the adjustment of the diameter of the ring pattern 71. On the other hand, it is also possible to input the ring pattern 71 via the keyboard 73.

In addition to the manual adjustments depicted hereinbefore for the position of the center of the preference pattern and its diameter or/and the position of the center of the ring pattern and its diameter, respectively, an automatic procedure can be also applied, which by an image processing recognizes the inner margin of the iris and makes the adjustments automatically.

In the embodiment described hereinbefore, the semitransparent mirror 41 is disposed in the partial beam bundle 61 to feed out the beam bundle 43 and produce an image of the object plane 9 through the camera chip 47, while the semitransparent mirror 61 is disposed in the partial beam bundle 24 to feed the pattern shown by display means 57 into the beam path of the microscopy optics 5. It is also possible, however, to provide both semitransparent mirrors 41 and 61 in only one of the partial beam bundles 23 or 24.

Also, it is possible that the ring pattern be faded in both partial beam bundles 23, 24 in particular such that the viewer gets a stereomicroscopic impression of the ring pattern in the object plane or possibly somewhat above or below.

In the embodiment described hereinbefore, the surgeon performs the operation while looking through the two oculars 25 and 26 of the microscopy optics 5. However, it is also possible that the surgeon performs the operation, while observing the operation field, i.e. object plane 9, on the screen 49.

Furthermore, it is possible that the controller 31 also supplies the image supplied to the screen 49 to a display means fixedly mounted on the surgeons head and referred to as "head mounted display". In this case, the surgeon receives an image of the operation field and the patterns generated by the pattern generator 63 in an ergonomic manner, without being tied down by the arrangement of the microscopy optics in respect of the position of his head.

Therefore, while the present invention has been shown and described herein in what is believed to be the most practical and preferred embodiments, it is recognized that departures can be made therefrom within the scope of the invention, which is therefore not be limited to the details disclosed herein but is to be accorded the full scope of the claims so as to embrace any and all equivalent methods and apparatus.

The invention claimed is:

1. A cataract surgery microscopy system comprising:
a microscopy optics including an objective lens and an ocular for generating an image of an object plane of said microscopy optics, wherein a semitransparent mirror is disposed in a beam path between said objective lens and said ocular; and
a pattern generator for generating a pattern superimposed on said image, said pattern generator being configured to generate a ring pattern with at least one adjustable diameter, wherein said pattern generator includes a display to display said pattern and a projector to project said pattern displayed on said display towards said ocular via said semitransparent mirror.

2. The cataract surgery microscopy system according to claim 1, wherein said pattern generator comprises an interface for inputting the at least one diameter of said ring pattern.

3. The cataract surgery microscopy system according to claim 2, wherein said microscopy optics is a microscopy optics of adjustable magnification and said pattern generator is coupled to said microscopy optics and configured such that the diameter of said ring pattern is adjustable in dependence of the adjusted magnification.

4. The cataract surgery microscopy system according to claim 1, wherein said pattern generator is configured to generate a reference pattern comprising a plurality of subpatterns, each of which is spaced an equal adjustable distance from a center of said reference pattern.

5. The cataract surgery microscopy system according to claim 4, wherein said center of said reference pattern is fixedly disposed with respect to a central point of said ring.

6. The cataract surgery microscopy system according to claim 4, wherein said pattern generator comprises an interface for inputting said distance.

7. The cataract surgery microscopy system according to claim 6, wherein said interface is provided with an actuator to be actuated by a user and mounted on a housing body of said microscopy optics.

8. The cataract microscopy system of claim 1, wherein said at least one adjustable diameter is user selectable.

9. The cataract microscopy system of claim 1, wherein said ring pattern represents an extension of a cut to be introduced into the skin of a capsule sac of the eye.

10. A cataract surgery microscopy system comprising:
a microscopy optics configured to generate an image of an object plane of said microscopy optics;
a camera configured to detect said image generated by said microscopy optics; and
a display configured to display said image detected by said camera; and
a pattern generator for generating a ring pattern with at least one adjustable diameter, wherein said pattern generator is configured to display said generated ring pattern on said display in superposition with said image detected by said camera.

11. The cataract surgery microscopy system according to claim 10, wherein said pattern generator comprises an interface for inputting said at least one diameter of said ring pattern.

12. The cataract surgery microscopy system according to claim 11, wherein said microscopy optics is a microscopy optics of adjustable magnification and said pattern generator is coupled to said microscopy optics and configured such that said diameter of said ring pattern is adjustable in dependence of said adjusted magnification.

13. The cataract surgery microscopy system according to claim 10, wherein said pattern generator is configured to generate a reference pattern comprising a plurality of subpatterns, each of which is spaced an equal adjustable distance from a center of said reference pattern.

14. The cataract surgery microscopy system according to claim 13, wherein said center of said reference pattern is fixedly disposed with respect to a central point of said ring.

15. The cataract surgery microscopy system according to claim 13, wherein said pattern generator comprises an interface for inputting said distance.

16. The cataract surgery microscopy system according to claim 15, wherein said interface is provided with an actuator to be actuated by a user and mounted on a housing body of said microscopy optics.

17. The cataract microscopy system of claim 10, wherein said at least one adjustable diameter is user selectable.

18. The cataract microscopy system of claim 10, wherein said ring pattern represents an extension of a cut to be introduced into the skin of a capsule sac of the eye.

19. The cataract surgery microscopy system according to claim 10.

20. The cataract surgery microscopy system according to claim 10, wherein said microscopy optics comprises an ocular for displaying said image generated by said microscopy optics and said ring pattern superimposed on said image.

* * * * *

UNITED STATES PATENT AND TRADEMARK OFFICE
CERTIFICATE OF CORRECTION

PATENT NO. : 7,784,947 B2 Page 1 of 1
APPLICATION NO. : 10/459858
DATED : August 31, 2010
INVENTOR(S) : Michel Pérez et al.

It is certified that error appears in the above-identified patent and that said Letters Patent is hereby corrected as shown below:

At Column 8, Claim 19, Line 56, after "The cataract surgery microscopy system according to claim 10" but before the "." please add --, wherein said display comprises a head mounted display--

Signed and Sealed this

Seventh Day of December, 2010

David J. Kappos
*Director of the United States Patent and Trademark Office*